United States Patent [19]
Johnson et al.

[11] Patent Number: 6,051,208
[45] Date of Patent: Apr. 18, 2000

[54] IN VIVO MAGNETIC RESONANCE VASCULAR IMAGING USING LASER-POLARIZED GAS MICROBUBBLES

[75] Inventors: G. Allan Johnson, Chapel Hill, N.C.; Mark S. Chawla, St. Clairsville, Ohio

[73] Assignee: Duke University, Durham, N.C.

[21] Appl. No.: 09/288,212

[22] Filed: Apr. 8, 1999

Related U.S. Application Data

[60] Provisional application No. 60/081,488, Apr. 13, 1998.

[51] Int. Cl.[7] .................................................. A61B 5/055
[52] U.S. Cl. ............................................ 424/9.3; 600/420
[58] Field of Search .............................. 424/9.3; 600/420

[56] References Cited

U.S. PATENT DOCUMENTS

| | | | |
|---|---|---|---|
| 5,785,953 | 7/1998 | Albert et al. | 424/9.3 |
| 5,809,801 | 9/1998 | Cates, Jr. et al. | 62/637 |

FOREIGN PATENT DOCUMENTS

95/27438  10/1995  WIPO .

OTHER PUBLICATIONS

In vivo magnetic resonance vascular imaging using laser–polarized $^3$He microbubbles; Mark S. Chawla, et al; Proc. Natl. Acad. Sci. USA; vol. 95, pp. 10832–10835, Sep. 1998, Medical Sciences.

Biological magnetic resonance imaging using laser–polarized $^{129}$Xe; M.S. Albert, et al.; Department of Chemistry, State University of New York, Stony Brook, New York 11794–3400, USA; Department of Physics, Princeton University, Princeton, New Jersey 08544, USA; Letters of Nature, pp. 199–201 Jul. 1994.

MR Imaging with Hyperpolarized $^3$He Gas; Hunter Middleton, et al., MRM 33:271–275 (1995); Department of Physics, Princeton University, Princeton, NJ; Depts. Of Biomedical Engineering and Physics, Duke University, Durham, NC; pp. 271–275.

In Vivo He–3 MR Images of Guinea Pig Lungs; Robert D. Black, et al., Technical Developments and Instrumentation; Center for in Vivo Microscopy, Duke University, pp. 867–870 (1996).

In Vivo MR Imaging and Spectroscopy Using Hyperpolarized $^{129}$Xe; Mark E. Wagshul, et al.; MRM 36:183–191 (1996); Depts. Radiology and Chemistry.

NMR of laser–polarized xenon in human blood (optical pumping/laser–polarized xenon); A. Bifone et al.; Proc. Natl. Acad. Sci. USA, vol. 93, pp. 12932–12936, Nov. 1996, Biophysics.

In vivo NMR and MRI using injection delivery of laser–polarized xenon; B.M. Goodson et al.; Proc. Natl. Acad. Sci. USA, vol. 94, pp. 14725–14729, Dec. 1997, Medical Sciences.

Brain MRI with Laser–Polarized $^{129}$Xe; Scott D. Swanson et al.; MRM 38:695–698 (1997).

Solubility of inert gases in biological fluids and tissues: a review; P.K. Weathersby and L.D. Homer, Naval Medical Research Institute, Bethesda, MD 20014; pp. 277–296 (1980).

Polarization of the nuclear spins of noble–gas atoms by spin exchange with optically pumped alkali–metal atoms; W. Happer, et al; Department of Physics, Princeton University, Princeton, NJ 08544 © 1984 The American Physical Society; pp. 3092–3110 (1984).

(List continued on next page.)

*Primary Examiner*—Gary E. Hollinden
*Attorney, Agent, or Firm*—Nixon & Vanderhye P.C.

[57] ABSTRACT

Nuclear magnetic resonance (NMR) images of a human or animal subject's vascular system are enhanced by injecting a liquid comprised of a biocompatible liquid carrier and a dispersion of hyperpolarized gas microbubbles into the subject, followed by generating an image by NMR representing a spatial distribution of the hyperpolarized gas microbubbles injected into the human or animal subject's vascular system. Preferably, the hyperpolarized gas is Helium-3 and/or Xenon-129. The microbubbles most preferably have a mean diameter of less than about 35 $\mu$m.

12 Claims, 3 Drawing Sheets

OTHER PUBLICATIONS

Polarized, high–density, gaseous $^3$He targets; T.E. Chupp et al; Physical Review C, vol. 36, No. 6, Dec. 1987, pp. 2244–2251.

Nuclear relaxation of $^3$He in the presence of $O_2$; B. Saam, et al., Physical Review A, vol. 52, No. 1, Jul. 1995; pp. 862–865.

Myocardial Contrast Echocardiography: A Reproducible Technique of Myocardial Opacification for Identifying Regional Perfusion Deficits; Chuwa Tel, M.D., et al.; Dept. of Medicine, Univ. of California School of Medicine, Wadsworth Veterans Administration Medical Center and Cedars–Sinai Medical Center, Los Angeles, CA; pp. 585–593 (1983).

Dynamics of Magnetization in hyperpolarized Gas MRI of the Lung; C. Allan Johnson, et al.; MRM 38:66–71 (1997).

MR Microscopy of Lung Airways with Hyperpolarized $^3$He; X. Josette Chen, et al; MRM 39:79–84 (1998).

Three–Dimensional Time–of–Flight Magnetic Resonance Angiography Using Spin Saturation; C.L. Dumoulin et al; General Electric Research and Development Center; MRM 11:35–46 (1989).

Mirobubble Dynamics Visualized in the Intact Capillary Circulation; StevenB. Feinstein, MD, et al.; JACC, vol. 4, No. 3, Sep. 1984, 595–600.

Nuclear Magnetic Resonance Imaging of Airways in Humans with Use of Hyperpolarized $^3$He; Peper Bachert, et al; MRM 36:192–196 (1996).

Contrast Echyocardiography; J.W. Winkelmann, et al.; University of Illinois at Chicago, Chicago, IL, pp. 507–515 (1994).

Principles and Practice of Nuclear Medicine; Paul J. Early et al.; Second Edition; pp. 376–420 (1995).

A Rapid–Gated Cine MRI Technique; Gary H. Glover et al.; Magnetic Resonance Annual 1988; pp. 299–333.

IN VIVO MAGNETIC RESONANCE VASCULAR IMAGING USING LASER-POLARIZED GAS MICROBUBBLES

This application claims the benefit of U.S. Provisional Application No. 06/081,488, filed Apr. 13, 1998.

GOVERNMENT RIGHTS STATEMENT

This invention was made with Government support under Grant No. 5P41 RR05959 awarded by the National Institutes of Health. The Government has certain rights in the invention.

FIELD OF THE INVENTION

The present invention relates generally to magnetic resonance imaging (MRI), and more specifically, to MRI techniques using laser-polarized gases. In preferred forms, the present invention is embodied in techniques whereby injectable liquid suspensions of laser-polarized gas microbubbles are employed to enhance vascular magnetic resonance images.

BACKGROUND AND SUMMARY OF THE INVENTION

High signal magnetic resonance (MR) images of void spaces, notably the lungs, have been acquired using laser-polarized or hyperpolarized noble gases, such as Xenon-129 and/or Helium-3. (See, U.S. Pat. No. 5,545,396, the entire content of each being expressly incorporated hereinto by reference, and References 1–4). Xenon-129 has also been used as a probe for blood, muscle, and brain tissue. (References 5–7). These studies rely on xenon dissolving in a carrier, such as lipid vesicles or blood. Since helium is 10–100 times less soluble than xenon in such materials (Reference 8), Helium-3 has been used exclusively for imaging air spaces. However, considering that the signal of Helium-3 is over 10 times greater than that of Xenon-129 for presently attainable polarization levels, it would be highly desirable to discover some means by which Helium-3 could be introduced into the vascular system. According to the present invention, such means are provided.

Broadly, the present invention is embodied in introducing a hyperpolarized noble gas (e.g., Helium-3 and/or Xenon-129) into a human or animal vascular system in the form of an injectable liquid containing microbubbles of the hyperpolarized gas dispersed or suspended in a biologically compatible carrier liquid. The techniques of the present invention allow for a potential increase in signal, and absence of background thereby permitting high resolution MR images to be obtained of human or animal vascular systems (i.e., angiographic images).

These and other aspects and advantages of the present invention will become more clear after careful consideration is given to the detailed description of the preferred exemplary embodiments thereof which follow.

BRIEF DESCRIPTION OF THE ACCOMPANYING DRAWINGS

Reference will hereinafter be made to the accompanying FIGURES wherein,

FIG. 3b is a $^1H$ image acquired with a standard time-of-flight angiographic pulse sequence for comparison against the image of FIG. 3a.

DETAILED DESCRIPTION OF THE INVENTION

The injectable hyperpolarized gas suspensions of this invention necessarily contain a biocompatible liquid carrier and microbubbles of a hyperpolarized noble gas. In this regard the carrier may be virtually any biocompatible liquid medium possessing minimal (if any) pharmacological effects and capable of containing sufficient amounts of the hyperpolarized gas microbubbles to produce the necessary SNR for in vivo MR imaging. Thus, according to the present invention conventional radiographic contrast agents (e.g., Hexabrix®, Renografin®, Isovue® and Omnipaque® contrast agents) and plasma volume expanders (e.g., Dextran and Heastarch) may be employed as the liquid carrier. When employing Helium-3 as the hyperpolarized gas, it is presently preferred to employ Hexabrix® radiographic contrast agent commercially available from Mallinckrodt Medical since it exhibits higher relative SNR (i.e., 1.00±0.19) as compared to the other carriers. In this regard, the preferred carrier is an iodine-based mixture containing ioxaglate meglumine (approx. 39.3%) and ioxaglate sodium (approx. 19.6%), and a minor amount of edetate calcium disodium, and exhibits a viscosity of about 15.7 cP at 20° C., a specific gravity of about 1.350 and a pH of 6–7.6.

The noble gas that is employed in the present invention is selected from noble gas isotopes having nuclear spin, preferably Helium-3 and/or Xenon-129. The noble gas may be hyperpolarized by any conventional technique (U.S. Pat. No. 5,642,625, the entire content of which is expressly incorporated hereinto by reference, and References 2, 9 and 10). Thus, the gas that is employed in the present invention is preferably one capable of being hyperpolarized by optical (laser) pumping in the presence of an alkali metal or by metastability exchange. That is, valence electrons in a Rb vapor may be optically pumped with circularly polarized laser light. Through collisional spin exchange, angular momentum is transferred to the noble gas nuclei.

Figure 1:
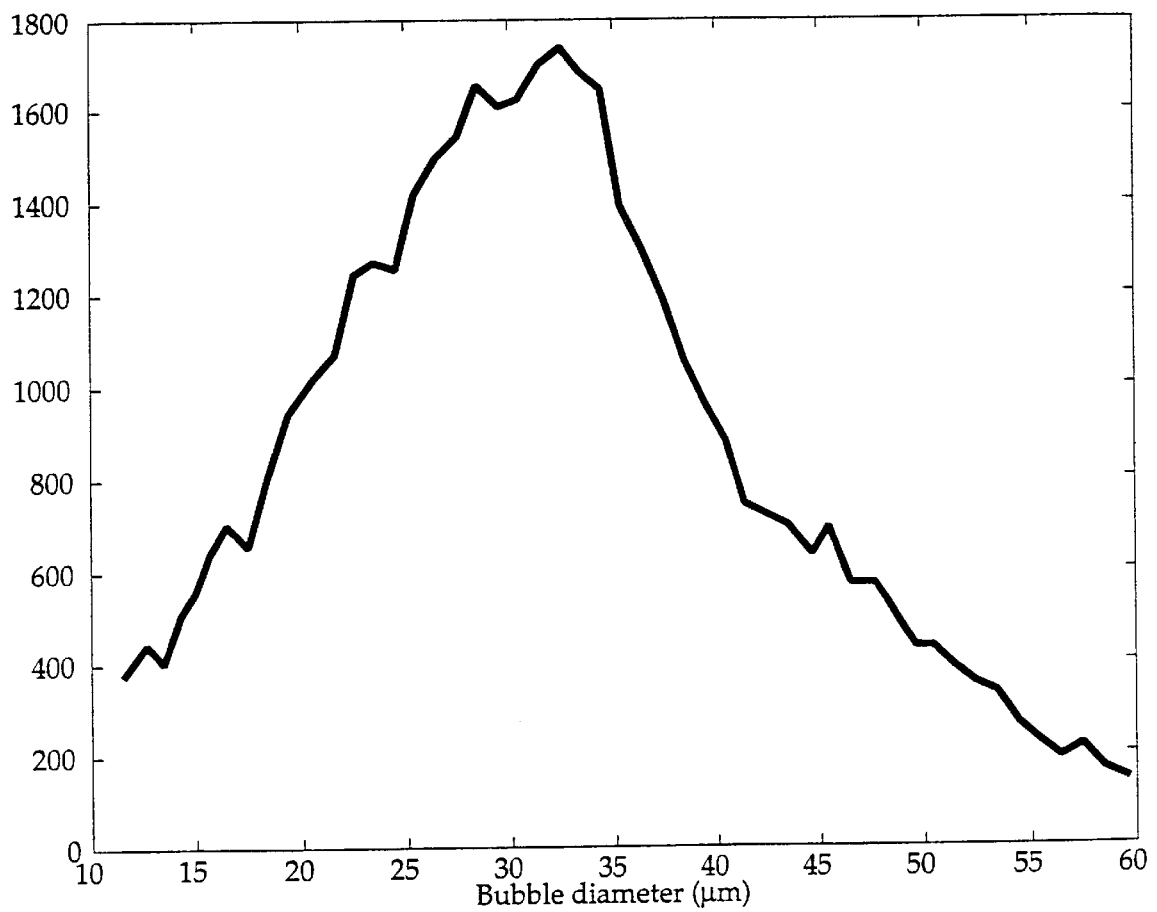
FIG. 1 is a graph of the approximate size distribution of Helium-3 microbubbles suspended in a conventional radiographic contrast agent.

Preferably, the injectable microbubble suspensions in accordance with the present invention are formed by introducing a previously hyperpolarized noble gas into a suitable carrier liquid and then vigorously agitating the mixture to form microbubbles suspended in the carrier liquid. The agitation that is employed is of sufficient intensity to achieve a mean microbubble diameter of less than about 35 μm, and usually about 32 μm. Most preferably, the mean microbubble diameter will be less than about 10 μm, and typically less than about 8 μm, which is approximately the size of a blood cell. Such a size will allow the safe passage of the microbubbles through the pulmonary circulation (Reference 13). According to Stokes' Law, characteristics of the suspending liquid carrier, including surface tension, density, and viscosity, affect the microbubble size distribution and the rate at which the microbubbles rise to the surface. The size distribution of the microbubbles suspended in Hexabrix® contrast agent was determined using a Coulter Counter (FIG. 1).

The concentration of hyperpolarized gas microbubbles in the liquid carrier is sufficient to allow MR signal acquisition over the time that imaging is conducted. To enhance image quality, it is essential to preserve the $^3He$ polarization while the microbubbles are suspended and prepared for injection.

Due to its nonequilibrium nature, magnetization decays with a characteristic time (longitudinal relaxation time or $T_1$) that depends on its surrounding environment. Additionally, signal loss occurs if the microbubbles physically rise out of the liquid carrier before injection of the suspension. Measurement of the combined effects of depolarization and rising bubbles in a phantom yielded an effective decay time of 41.6±8.7 seconds for Hexabrix® radiographic contrast agent. This value is a lower limit of the actual $T_1$ and indicates adequate magnetization will persist throughout the mixing and delivery process. The time constant for the decay of the MR signal obtained from each radio frequency (RF) excitation is known as $T_2^*$. By measuring the linewidth of the Fourier transformed signal in the $^3$He bubbles, it was found that $T_2^* \cong 20$ ms.

A further understanding of this invention will be obtained from the following non-limiting Examples.

EXAMPLES $^3$He was polarized to 10–15% by the spin exchange method (Reference 2). 2 cm$^3$ of $^3$He was withdrawn into an evacuated 10 cm$^3$ plastic syringe. This syringe was then connected, via a plastic three-way stopcock, to a second 10 cm$^3$ syringe containing 8 cm$^3$ of liquid carrier. Rapidly flushing the fluids several times between syringes produced a suspension of $^3$He microbubbles.

Imaging was performed on a 2.0 T, 30-cm-bore Oxford magnet with shielded gradients using a GE signa console and a 7-cm-diameter dual-frequency ($^3$He and $^1$H) birdcage coil.

In vivo imaging was performed with male Sprague-Dawley rats (400–480 g) that were anesthetized with either pentobarbital sodium or isoflurane. For venous injections, a 22-gauge plastic cannula was inserted into a lateral tail vein, whereas for arterial injections, a catheter (PE 50 tubing) was inserted into the aorta via the carotid artery. Immediately after creating the $^3$He microbubble suspension, 7 cm$^3$ were injected over a period of either 10 or 26 seconds during which imaging occurred.

The animal was placed in the supine position inside a dual-frequency, 7-cm-diameter birdcage RF coil operating at 64.8 MHz and 85.5 MHz for $^3$He and $^1$H, respectively. All $^3$He imaging employed a standard 2D gradient-recalled echo pulse sequence (Reference 20) with the following parameters: 79 mm field-of-view (FOV), 128×256 matrix size zero-filled to 256×256, and 1.2 ms effective echo time (TE). Both images in FIGS. 2a and 2b used an 80 ms repetition time (TR) and 20° flip angle ($\alpha$), while FIG. 3a was obtained with a 200 ms TR and 15° $\alpha$. The 3D $^1$H image (FIG. 3b) was acquired using a vascular time-of-flight sequence (Reference 15) with 79 mm FOV, 192×256 matrix size zero-filled to 256×256, 2.2 ms TE, 18 ms TR, 30°$\alpha$, 2 excitations, and 0.7 mm slice thickness. RF pulses associated with image acquisition necessarily depolarized the $^3$He. As a result, the RF power (i.e., flip angle), repetition time, and injection rate were carefully chosen to ensure that sufficient magnetization would remain throughout the region of interest (References 13–14).

Figure 2A:
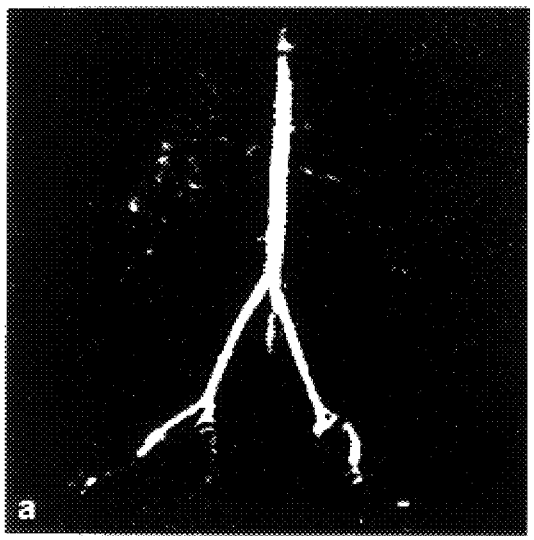
FIGS. 2a and 2b are MR images of rat pelvic arteries and veins, respectively, obtained using Helium-3 microbubbles.
Figure 2B:
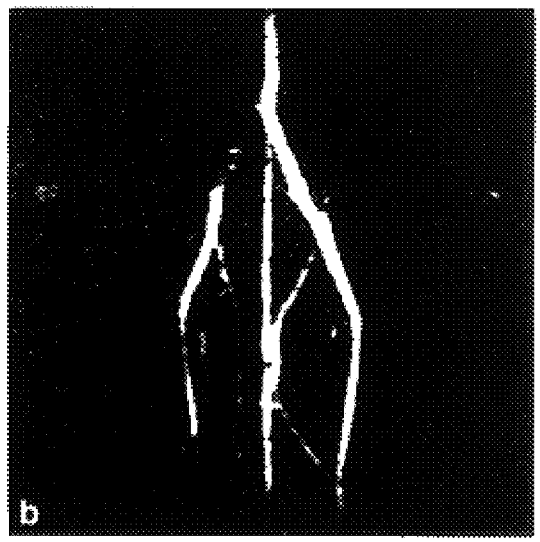

Images of both the arteries and veins of the rat pelvic region obtained using $^3$He microbubbles suspended in Hexabrix® are shown in accompanying FIGS. 2a and 2b, respectively. Excellent delineation of all major vessels can be seen, with a maximum SNR≅55 in both images. Observable blood vessels include the abdominal aorta, common iliac, and external iliac arteries in FIG. 2a, and the vena cava, common iliac, and caudal veins in FIG. 2b.

Figure 3A:
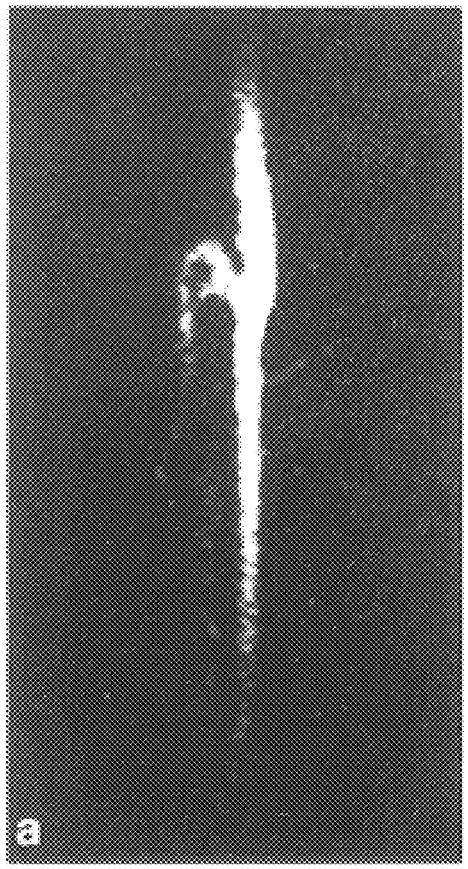
FIG. 3a is a Helium-3 MR image of a rat abdominal aorta and renal arteries.
Figure 3B:

A $^3$He image of the abdominal aorta and renal arteries is shown in FIG. 3a. In the lower portion of this image, a faint line runs parallel with the aorta. It is believed that the faint line is an image of the vena cava, based on the anatomy depicted in a corresponding proton image acquired with a standard time-of-flight angiographic pulse sequence (FIG. 3b) (Reference 15). This means sufficient amounts of polarized $^3$He bubbles reached the venous circulation. The absence of the vena cava in FIG. 2a is probably a result of depolarization caused by using a larger flip angle and a shorter repetition time.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

ADDENDUM OF REFERENCES

The Entire Content of Each Reference Cited Below is Expressly Incorporated Hereinto by Reference.

1. Albert, M. S. et al. Biological magnetic resonance imaging using laser-polarized $^{129}$Xe, *Nature* 370,199–201 (1994).
2. Middleton, H. et al. MR imaging with hyperpolarized $^3$He gas, *Magn. Reson. Med.* 33, 271–275 (1995).
3. Black, R. D. et al. In vivo He-3 MR images of guinea pig lungs, *Radiol* 199, 867–870 (1996).
4. Wagshul, M. et al. In vivo MR imaging and spectroscopy using hyperpolarized $^{129}$Xe, *Magn. Reson. Med.* 36, 183–191 (1996).
5. Bifone, A. et al. NMR of laser-polarized xenon in human blood, *Proc. Natl. Acad. Sci. USA* 93, 12932–12936 (1996).
6. Goodson, B. M. et al. In vivo NMR and MRI using injection delivery of laser-polarized xenon, *Proc. Natl. Acad. Sci. USA* 94, 14725–14729(1997).
7. Swanson, S. D. et al. Brain MRI with laser-polarized $^{129}$Xe, *Magn. Reson. Med.* 38, 695–698 (1997).
8. Weathersby, P. K. & Homer, L. D. Solubility of inert gases in biological fluids and tissues: a review, *Undersea Biomed. Res.* 7, 277–296 (1980).
9. Happer, W. et al. Polarization of the nuclear spins of noble-gas atoms by spin exchange with optically pumped alkali-metal atoms, *Phys. Rev. A* 29, 3092–3110 (1984).
10. Chupp, T., Wagshul, M., Coulter, K., McDonald, A. & Happer, W. Polarized high-density gaseous $^3$He targets, *Phys. Rev. C* 36, 2244–2251(1987).
11. Saam, B., Happer, W. & Middleton, H. Nuclear relaxation of $^3$He in the presence of $O_2$, *Phys. Rev. A* 52, 862–865 (1995).
12. Tei, C. et al. Myocardial contrast echocardiography: a reproducible technique of myocardial opacification for identifying regional perfusion deficits, *Circulation* 67, 585–593 (1983).
13. Johnson, G. A. et al. Dynamics of magnetization in hyperpolarized gas MRI of the lung, *Magn. Reson. Med.* 38, 66–71 (1997).
14. Chen, X. J. et al. MR microscopy of lung airways with hyperpolarized $^3$He, *Magn. Reson. Med.* 39, 79–84 (1998).
15. Dumoulin, C. L., Cline, H. E., Souza, S. P., Wagle, W. A. & Walker, M. F. Three-dimensional time-of-flight magnetic resonance angiography using spin saturation, *Magn. Reson. Med.* 11, 35–46 (1989).

16. Feinstein, S. B. et al. Microbubble dynamics visualized in the intact capillary circulation, *J. Am. Coil. Cardiol.* 4, 595–600 (1984).
17. Bachert, P. et al. Nuclear magnetic resonance imaging of airways in humans with use of hyperpolarized $^3$He, *Magn. Reson. Med.* 36, 192–196 (1996).
18. Winkelmann, J. W., Kenner, M. D., Dave, R., Chandwaney, R. H. & Feinstein, S. B. Contrast echocardiography, *Ultrasound in Med. & Biol.* 20, 507–515 (1994).
19. Sodee, D. B. et al. in Principles and Practice of Nuclear Medicine (eds. Early, P. J. & Sodee, D. B.) 370–442 (Mosby, St. Louis, 1995).
20. Glover, G. H. & Pelc, N. J. A rapid-gated cine MRI technique, *Magn. Reson. Annual* 299–333 (1988).
21. Chawla, M. S. et al. The feasibility of vascular MR microscopy using hyperpolarized gas, Proc. ISMRM, 5th annual meeting, Vancouver, p. 2114 (1997).

What is claimed is:

1. A method of nuclear magnetic resonance (NMR) imaging of a vascular system of a human or animal subject comprising:
    (a) injecting a liquid comprised of a biocompatible liquid carrier and a dispersion of hyperpolarized gas microbubbles into the human or animal subject's vascular system; and then
    (b) generating an image by NMR representing a spatial distribution of said hyperpolarized gas microbubbles injected into the human or animal subject's vascular system.

2. The method of claim 1, wherein the hyperpolarized gas is a noble gas.

3. The method of claim 2, wherein the hyperpolarized noble gas is Helium-3 and/or Xenon-129.

4. The method of claim 1, further comprising prior to step (a), the step of mixing the liquid carrier and an NMR effective amount of the hyperpolarized gas under sufficient agitation conditions to achieve microbubbles of said hyperpolarized gas suspended in said liquid carrier.

5. The method of claim 1, wherein prior to said mixing step, there is practiced the step of subjecting a non-polarized noble gas to spin-exchange polarization to achieve a hyperpolarized noble gas.

6. The method of claim 5, wherein said step of subjecting the non-polarized noble gas to spin-exchange is practiced such that the noble gas is polarized between about 10% to about 15%.

7. The method of claim 1, wherein the microbubbles have a mean diameter of less than about 35 $\mu$m.

8. The method of any one of the preceding claims, wherein the method is practiced in vivo with a human or animal subject.

9. A biocompatible injectable liquid to enhance nuclear magnetic resonance (NMR) images of human or animal vascular systems comprising:
    (a) a biocompatible liquid carrier; and
    (b) a NMR enhancing effective amount of hyperpolarized noble gas microbubbles suspended in said liquid carrier.

10. The injectable liquid of claim 9, wherein the hyperpolarized noble gas is Helium-3 and/or Xenon-129.

11. The injectable liquid of claim 9 or 10, wherein the hyperpolarized noble gas microbubbles have a mean diameter of less than about 35 $\mu$m.

12. The injectable liquid of claim 9 or 10, wherein the hyperpolarized gas is spin-polarized between about 10% to about 15%.

* * * * *